(12) United States Patent
Chen

(10) Patent No.: US 6,961,374 B2
(45) Date of Patent: Nov. 1, 2005

(54) PULSE DATA CODING METHOD FOR WIRELESS SIGNAL TRANSMITTING AND RECEIVING DEVICES

(75) Inventor: Shui Jung Chen, Taipei (TW)

(73) Assignee: Direction Technology Co., Ltd., Taipei (TW)

(*) Notice: Subject to any disclaimer, the term of this patent is extended or adjusted under 35 U.S.C. 154(b) by 345 days.

(21) Appl. No.: 10/369,669

(22) Filed: Feb. 21, 2003

(65) Prior Publication Data

US 2004/0166911 A1 Aug. 26, 2004

(51) Int. Cl.[7] .............................................. H04K 7/08
(52) U.S. Cl. ..................................................... 375/238
(58) Field of Search ................................ 375/238, 259, 375/295, 377, 239, 340, 285, 296, 346, 316; 370/205; 341/60, 53; 340/870.24, 825.63

(56) References Cited

U.S. PATENT DOCUMENTS 6,092,722 A * 7/2000 Heinrichs et al. ........... 235/375
6,272,190 B1 * 8/2001 Campana, Jr. .............. 375/347
2003/0137403 A1 * 7/2003 Carrender et al. ......... 340/10.4

* cited by examiner

*Primary Examiner*—Tesfaldet Bocure
(74) *Attorney, Agent, or Firm*—Rosenberg, Klein & Lee

(57) ABSTRACT

A pulse data coding method for wireless signal transmitting and receiving devices includes the steps of using a transmitter to transmit a signal of pulse data to be transmitted, transmitting at least one identification code pulse signal after a predetermined time interval from the transmission of the pulse data signal, and transmitting a check code pulse signal after another predetermined time interval from the transmission of the identification code pulse signal. The check code pulse signal is obtained by coding the pulse data signal and the identification code pulse signal according to a predetermined coding process. When a corresponding receiver receives the signal from the transmitter, it determines a correctness of the received signal according to the predetermined coding process, which may be an algorithm of addition, subtraction, multiplication, division, and/or a ratio operation.

13 Claims, 11 Drawing Sheets

PULSE DATA CODING METHOD FOR WIRELESS SIGNAL TRANSMITTING AND RECEIVING DEVICES

BACKGROUND OF THE INVENTION

1. Field of the Invention

The present invention relates to a wireless signal transmitting and receiving technique, and more particularly to a pulse data coding method for wireless signal transmitting and receiving devices, with which a pulse data signal transmitted by a transmitting device is protected against interference by noise signals and can therefore be correctly received by a corresponding receiving device.

2. Description of the Prior Art

It is a common practice in many electronic apparatus to transmit a signal of the electronic apparatus to a nearby receiving device by means of wireless transmitting/receiving technique, so that the electronic apparatus is more practical for use without being limited by a signal wire or cable. For example, most of the currently very popular exercise apparatus include a sensor to detect the user's heart rate, so that a signal of the detected heartbeat rate is processed by a transmitter and wirelessly sent in the form of a heartbeat pulse signal to a nearby receiver via a radio carrier, enabling the user to timely and properly control his or her body condition while taking exercises.

In the conventional pulse data wireless transmitting and receiving techniques, the pulse data may be sent in several different forms, including single pulse, long duration pulse, dual pulse/multiple pulse, coded pulse, etc. FIG. 1 illustrates waveforms of a heartbeat signal S10 detected by a transmitter and transmitted in different forms of single pulse S11, long duration pulse S12, double pulse/multiple pulse S13, and coded pulse S14 through conventional wireless signal transmitting technique, and FIG. 2 shows different waveforms of the heartbeat signal S10 received by a receiver when the heartbeat signal S10 is transmitted in different forms of single pulse S11, long duration pulse S12, double pulse/multiple pulse S13, and coded pulse S14 through conventional wireless signal transmitting technique without being interfered by noise signals.

However, it is almost impossible to avoid interferences by noise signals in real application of the wireless transmitting and receiving techniques. FIG. 3 shows the waveforms of the heartbeat signal S10 received by a receiver when the pulse signal S10 is transmitted in different forms of single pulse S11, long duration pulse S12, double pulse/multiple pulse S13, and coded pulse S14 through conventional wireless signal transmitting technique under interferences by noise signals, which are generally denoted by Sn. When a pulse data signal is transmitted in the form of single pulse S11 using conventional wireless transmitting technique, a receiver interfered by noise signals Sn from, for example, a motor, a television set, an alternating power line, a computer, or a radio communication equipment, is completely not protected against such interferences with the transmitted signals, and could not correctly receive the signals transmitted by a corresponding transmitter.

When the pulse data signal is transmitted in the form of long duration pulse S12 using conventional wireless transmitting technique, it is possible to protect the long duration pulse signal S12 against part of existing noise signals. However, the receiver would not be able to avoid the interferences by the noise signals Sn when the noise signals Sn come from an interference source having a considerably high intensity. In addition, the long duration pulse S12 would disadvantageously consume higher power.

When the pulse data signal is transmitted in the form of dual pulse/multiple pulse S13 using conventional wireless transmitting technique, it is possible to protect the dual pulse/multiple pulse signal S13 against part of existing noise signals Sn. However, the receiver would not be able to discriminate real signals from false signals when the receiver is subjected to interferences from a continuous interference source, such as interference signals from an alternating power supply of 60 Hz or other frequencies.

When the pulse data signal is transmitted in the form of coded pulse S14 using conventional wireless transmitting technique over high-frequency carrier or ultrahigh-frequency carrier, the signal may usually be ideally transmitted. However, when the pulse data signal is transmitted in the form of coded pulse S14 using conventional wireless transmitting technique over low-frequency carrier, such as 5 KHz or 10 KHz, problems of insufficient bandwidth and high probability of signal corruption due to noise signals would exist. In addition, the transmission of pulse data signals in the form of coded pulse S14 also has the disadvantage of high power consumption and is therefore not an optimum way in transmitting pulse date signals.

SUMMARY OF THE INVENTION

It is therefore a primary object of the present invention to provide a pulse data coding method for wireless signal transmitting and receiving devices, so that the pulse data signals transmitted by the transmitting device is protected against interferences from noise signals and correctly received by a corresponding receiving device.

Another object of the present invention is to provide a pulse data coding method for wireless signal transmitting and receiving devices, so that pulse data may be correctly transmitted without being affected by different factors, including, for example, distance and angle between the transmitting and the receiving device, and/or a circuit response rate of the receiving device. Since the pulse data signal coded in the method of the present invention has a proportionably modulated pulse width, the receiving device may still determine the correctness of the received pulse data signal even if the pulse width of the transmitted pulse data signal is affected by the distance and angle between the transmitting and the receiving device, and/or the circuit response rate of the receiving device.

A further object of the present invention is to provide a pulse data coding method for wireless signal transmitting and receiving devices, so that pulse data signals may be transmitted with reduced power consumption. In the pulse data coding method of the present invention, only three pulse signals, namely, the pulse data signal, an identification code pulse signal, and a check code pulse signal, are used in transmitting the pulse data and checking a correct transmission thereof. Therefore, the present invention has the advantage of reduced power consumption as compared to the conventional pulse data transmitting method that uses a plurality of coded pulses.

To achieve the above objects, in accordance with the present invention, there is provided a pulse data coding method which includes the steps of using a transmitter to transmit a signal of pulse data to be transmitted, transmitting at least one identification code pulse signal after a first predetermined time interval from the transmission of the pulse data signal, and transmitting a check code pulse signal after a second predetermined time interval from the transmission of the identification code pulse signal. The check code pulse signal is obtained by coding the pulse data signal and the identification code pulse signal in accordance with a predetermined coding process. The receiver, on receipt of the coded pulse data signal transmitted by the transmitter, would check the check code pulse signal of the received signal according to the predetermined coding process to determine whether the received signal is a correct signal. The coding process may be, for example, an algorithm of addition (+), subtraction (−), multiplication (×), division (÷), or a ratio. Preferably, a waveform shaping circuit is included in the circuitry of the receiver to regulate the pulse width of the received pulse signal, so that the pulse signal received has a pulse width that is not too narrow.

BRIEF DESCRIPTION OF THE DRAWINGS

The technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
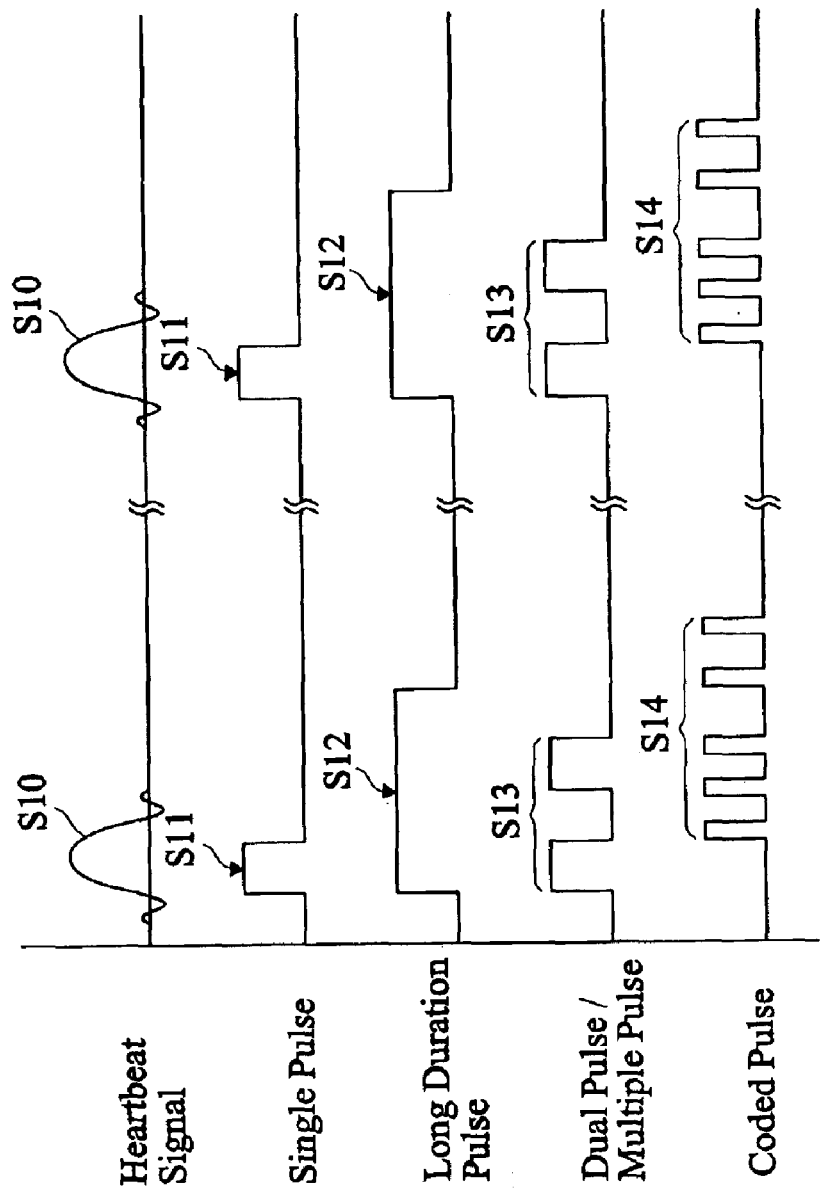
FIG. 1 illustrates different waveforms of a pulse signal transmitted in the forms of single pulse, long duration pulse, double pulse/multiple pulse, and coded pulse through conventional wireless signal transmitting technique.
Figure 2:
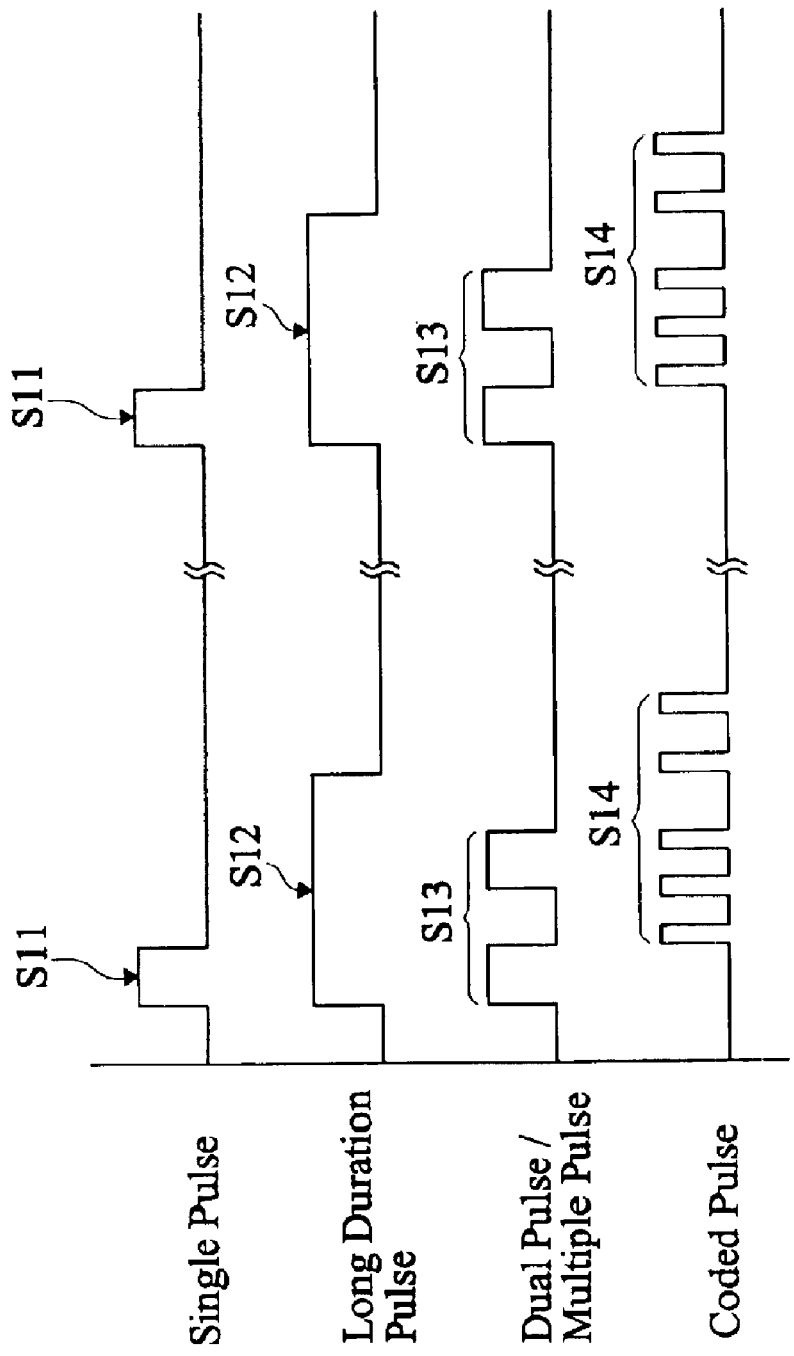
FIG. 2 shows the waveforms of a pulse signal received by a receiving device when the pulse signal is transmitted in the forms of single pulse, long duration pulse, double pulse/multiple pulse, and coded pulse through conventional wireless signal transmitting technique without being interfered by noise signals.
Figure 3:
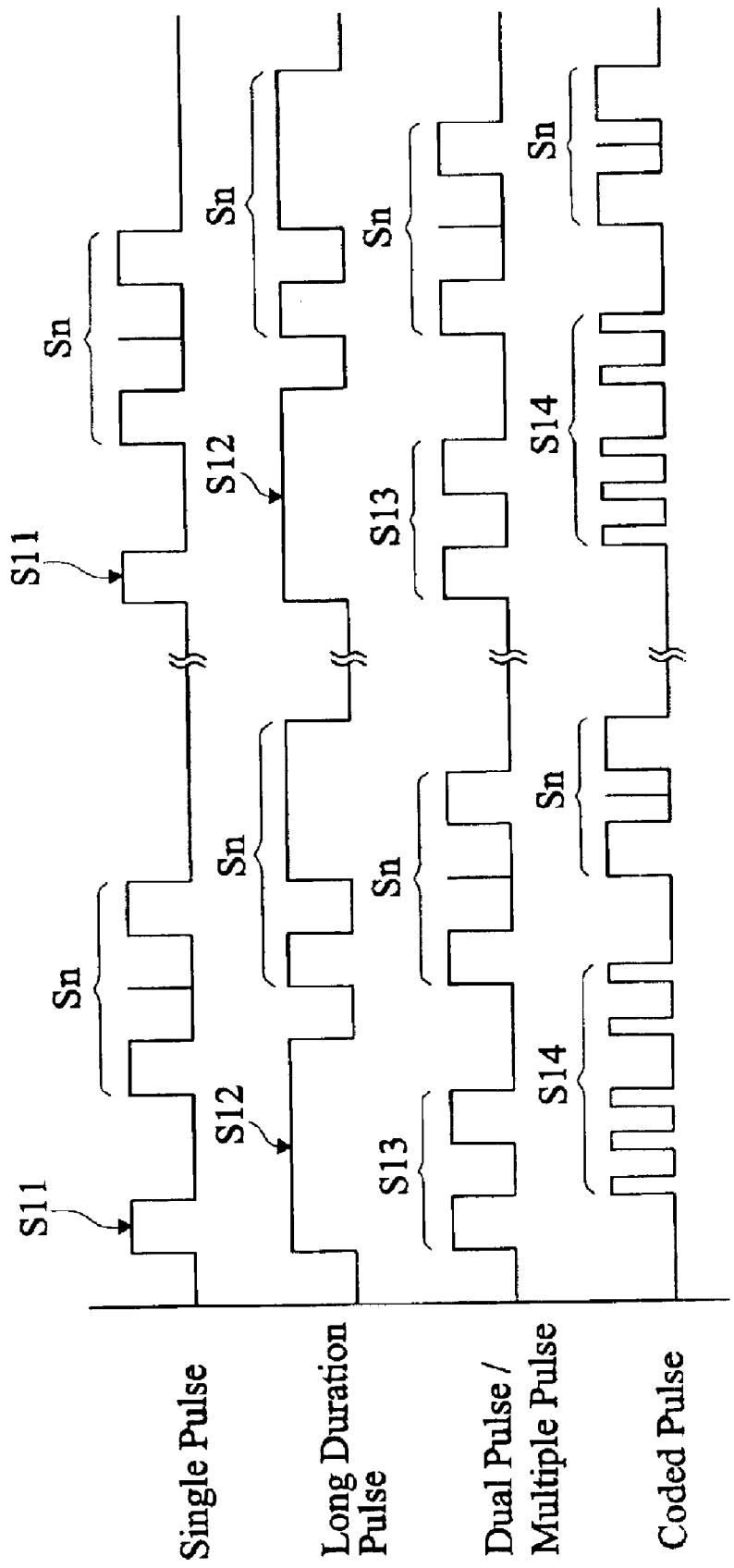
FIG. 3 shows the waveforms of a pulse signal received by a receiving device when the pulse signal is transmitted in the forms of single pulse, long duration pulse, double pulse/multiple pulse, and coded pulse through conventional wireless signal transmitting technique under interferences by noise signals.
Figure 4:
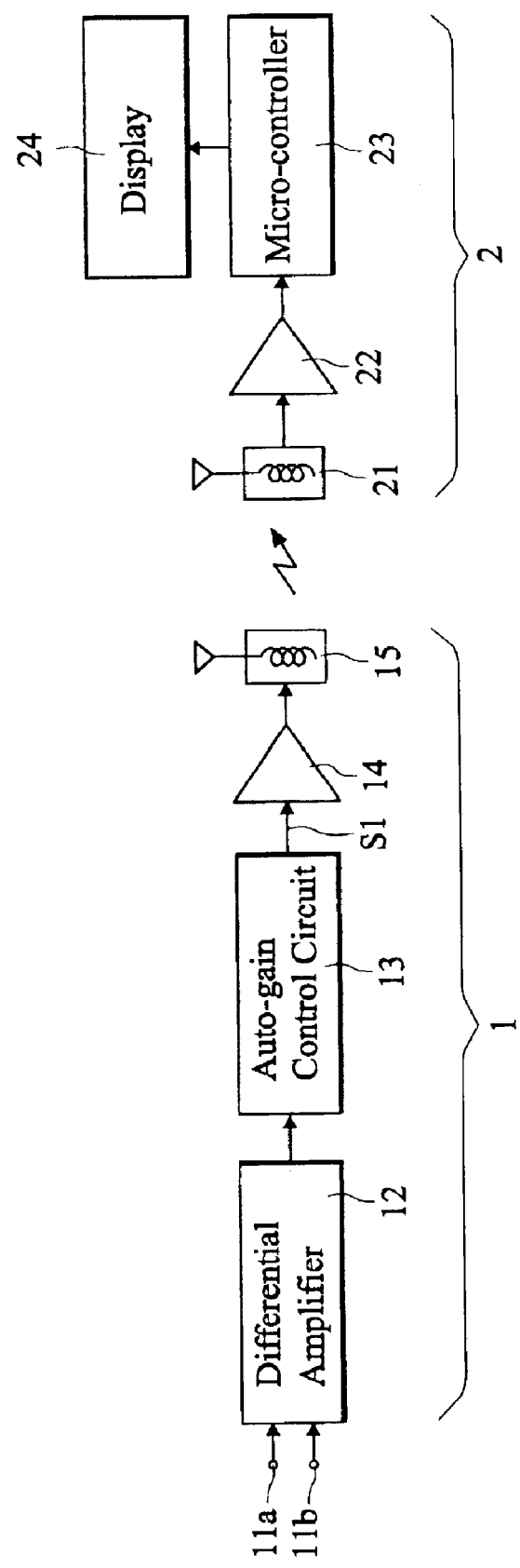
FIG. 4 is a functional block diagram showing the circuit of a wireless heartbeat signal transmitter/receiver employing the present invention.

Please refer to FIG. 4 that is a functional block diagram showing the circuit of a wireless heartbeat pulse signal transmitting/receiving device employing the present invention. As shown, the device includes a transmitter 1 and a receiver 2. The transmitter 1 mainly includes a pair of heartbeat pulse sensing electrodes 11$a$, 11$b$, a differential amplifier 12, an auto-gain control circuit 13, an amplification circuit 14, and a transmitting coil 15. And, the receiver 2 includes a receiving coil 21, an amplification circuit 22, a micro-controller 23, and a display 24.

When the heartbeat pulse sensing electrodes 11$a$, 11$b$ of the transmitter 1 detect a heartbeat pulse signal, the detected signal is caused to pass the differential amplifier 12 and the auto-gain control circuit 13 to obtain a pulse data signal S1, which is further amplified by the amplification circuit 14 before being transmitted by the transmitting coil 15 over a carrier signal and received by the receiving coil 21 of the receiver 2. The signal received by the receiver 2 is amplified by the amplification circuit 22 and then sent to the micro-controller 23, at where the signal is processed and converted into number of heartbeats for showing on the display 24.

Figure 5:
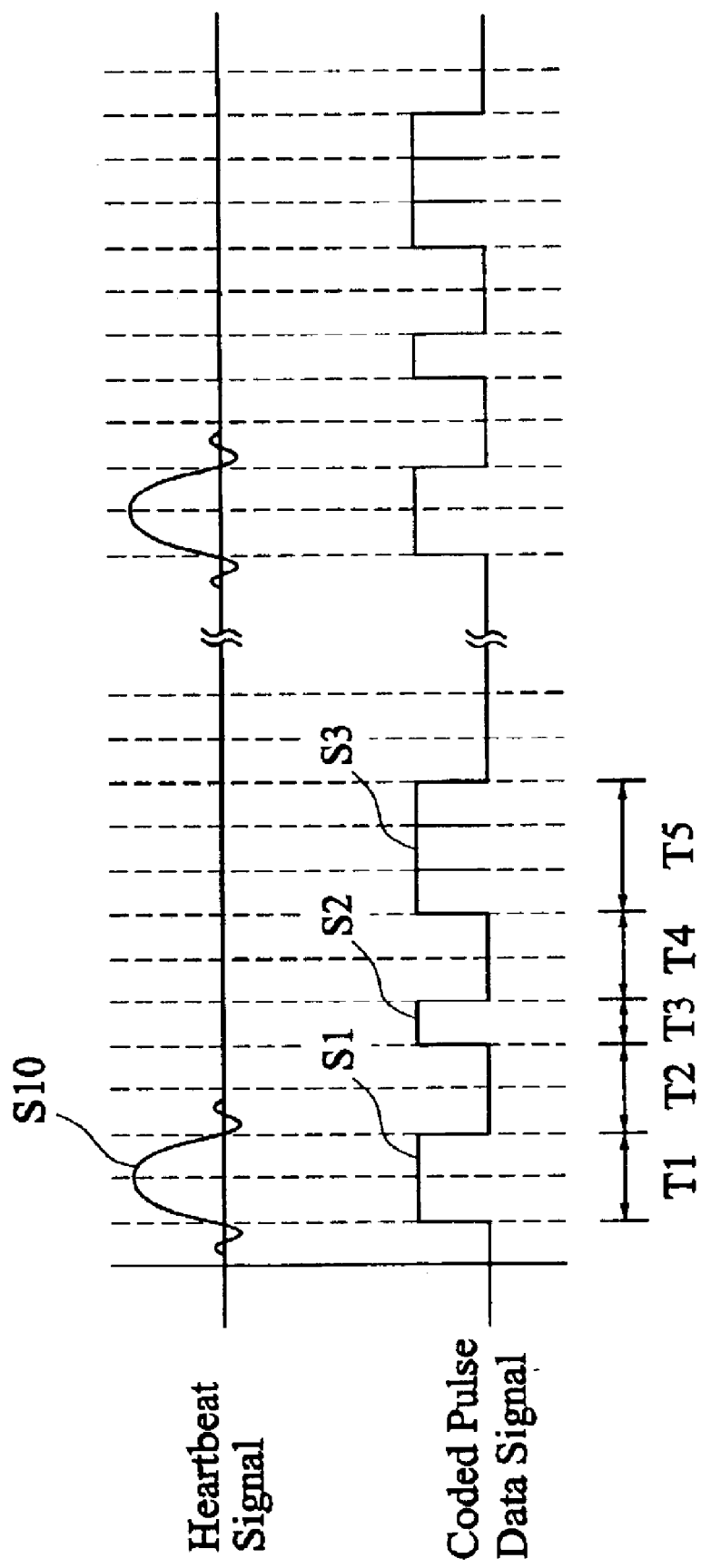
FIG. 5 shows a waveform of a pulse signal being transmitted in the form of a coded pulse signal according to a first embodiment of the present invention, wherein the coded pulse signal includes a check code pulse signal, which is obtained from an coding process of an algorithm of addition operation.

FIG. 5 shows the waveform of a pulse signal being transmitted in the form of a coded pulse signal that is coded in the pulse data coding method of the present invention. The following description of the pulse data coding method of the present invention is made based on the wireless heartbeat pulse signal transmitting/receiving device of FIG. 4. As shown, the detected heartbeat signal S10 is caused to pass the differential amplifier 12 and the auto-gain control circuit 13 of the transmitter 1 to obtain a series of pulse data signals S1, each of which has a pulse duration or pulse width T1.

When a pulse data signal S1 is transmitted by the transmitter 1, and a predetermined time interval T2 has lapsed from the transmission of the pulse data signal S1, an identification code pulse signal S2 having a pulse duration or pulse width T3 is immediately transmitted. Then, after another predetermined time interval T4 is lapsed from the transmission of the identification code pulse signal S2, a check code pulse signal S3 having a pulse width T5 is transmitted.

The check code pulse signal S3 is obtained by coding the pulse data signal S1 and the identification code pulse signal S2 in accordance with a predetermined coding process or coding protocol. The coding process may be, for example, an algorithm of addition (+), subtraction (−), multiplication (×), division (÷), or a ratio operation of the pulse data signal S1 and the identification code pulse signal S2. For instance, when the coding process for the check code pulse signal S3 is an algorithm of addition operation (+) in accordance with a first embodiment of the present invention, then the time data for the coded pulse data signal of the heartbeat signal S10 are as follows:

T1=10 ms
T2=10 ms
T3=5 ms
T4=10 ms
T5=T1+T3=10 ms+5 ms=15 ms.

In this embodiment, the check code pulse signal S3 has a pulse width T5 of 15 ms. Thus, the signal transmitted by the transmitter 1 and received at the receiver 2 end would be as follows:

T1=10 ms
T2=10 ms
T3=5 ms
T4=10 ms
T5=15 ms.

Since the receiver 2 and the transmitter 1 have been previously set to work under the same coding process or coding protocol, the receiver 2, on receipt of the coded pulse data signal transmitted by the transmitter 1, would check the check code pulse signal S3 of the received signal according to the predetermined coding process to determine whether the received signal is a correct signal.

Figure 6:
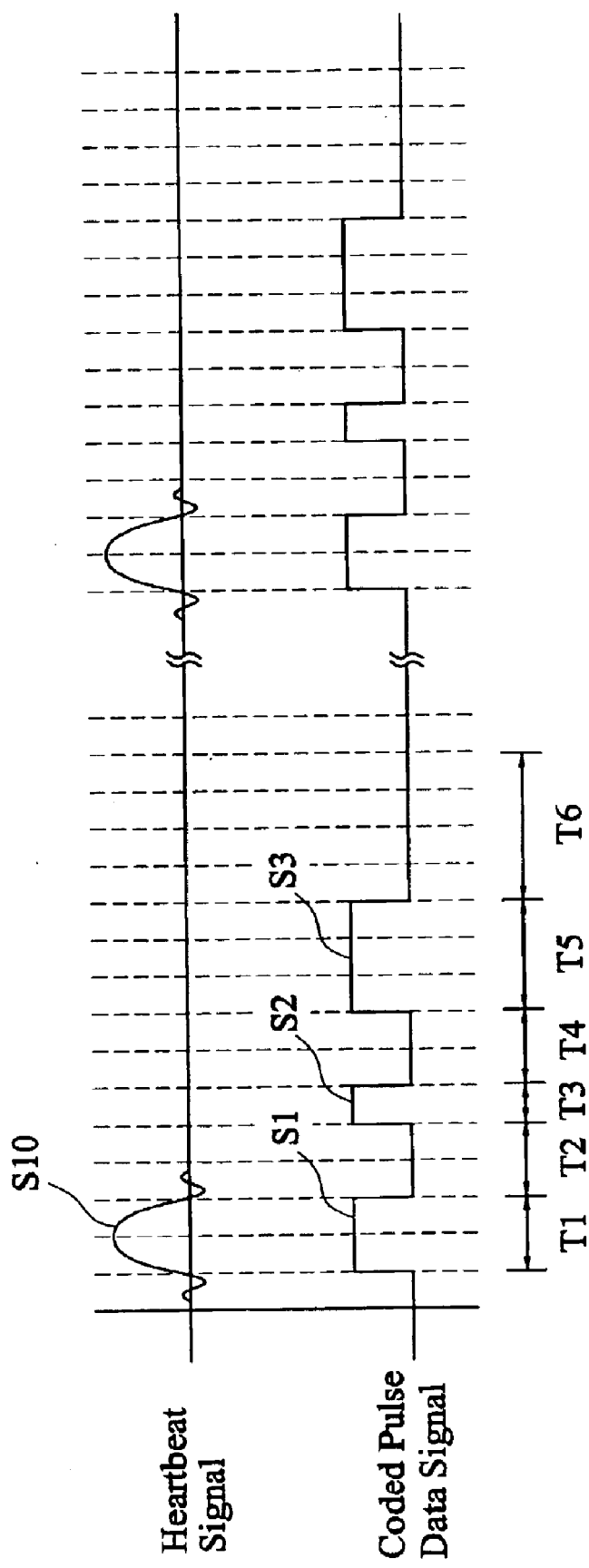
FIG. 6 shows a waveform of a pulse signal being transmitted in the form of a coded pulse signal according to a second embodiment of the present invention, wherein the coded pulse signal includes a check code pulse signal, which is obtained from an coding process of an algorithm of addition operation.

Alternatively, based on the algorithm of addition operation (+), the check code pulse signal S3 may be obtained by extendedly coding the pulse duration T1 of the pulse data signal S1, the time interval T2, the pulse duration T3 of the identification code pulse signal S2, and the time interval T4 in accordance with a second embodiment of the present invention. With reference to FIG. 6, in this embodiment, the time data for the coded pulse data signal of the heartbeat signal S10 are as follows:

T1=10 ms
T2=10 ms
T3=5 ms
T4=10 ms
T5=T1+T3=10 ms+5 ms=15 ms
T6=T2+T4=10 ms+10 ms=20 ms

That is, the pulse data coding processes of this embodiment comprises steps of summing the first pulse duration T1 of the pulse data signal S1 and the second duration T3 of the identification code pulse signal S2 to obtain a high state pulse width T5 of the check code pulse signal S3, and summing the first time interval T2 and the second time interval T4 to obtain a low state pulse width T6 of the check code pulse signal S3.

The signal transmitted by the transmitter 1 and received at the receiver 2 end would be as follows:

T1=10 ms
T2=10 ms
T3=5 ms
T4=10 ms
T5=15 ms
T6=20 ms

Figure 7:
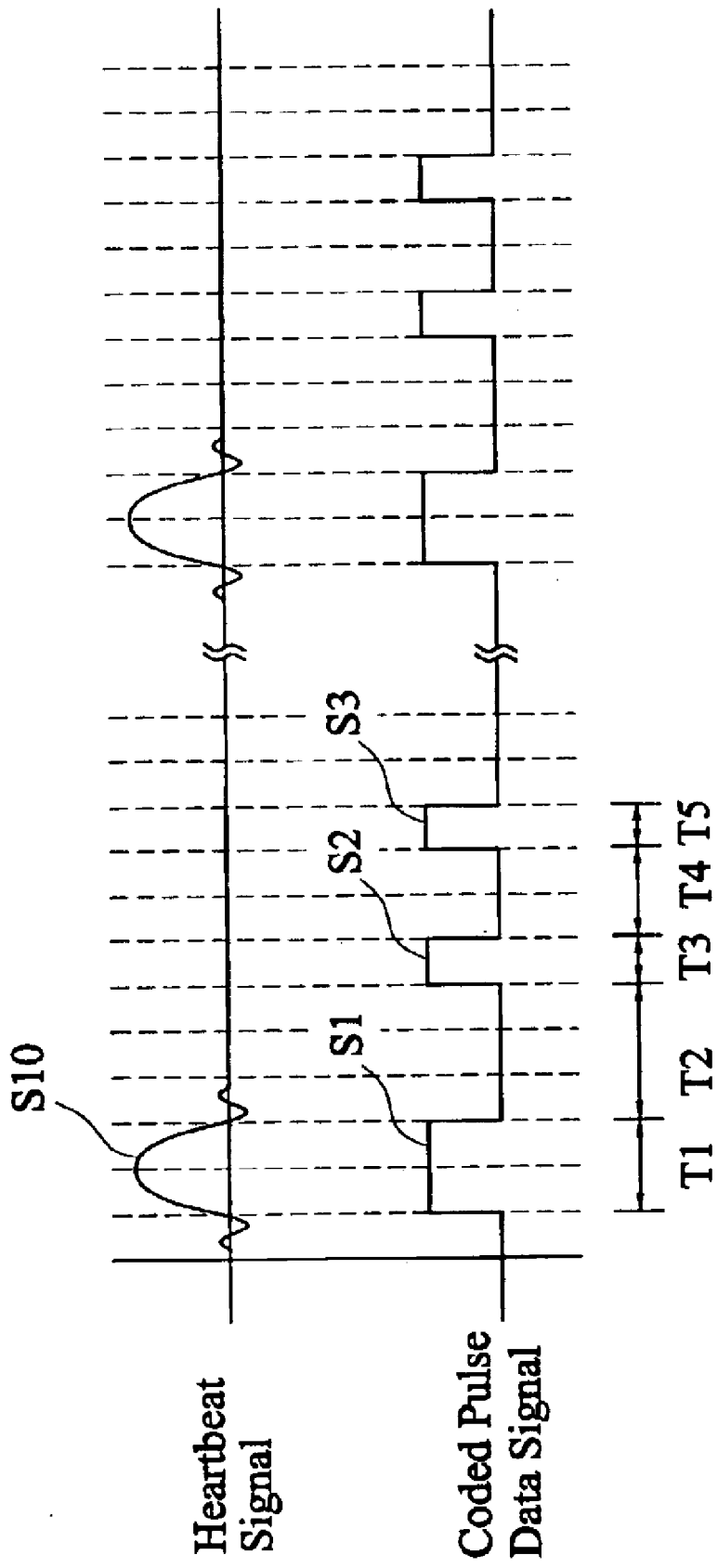
FIG. 7 shows a waveform of a pulse signal being transmitted in the form of a coded pulse signal according to a third embodiment of the present invention, wherein the coded pulse signal includes a check code pulse signal, which is obtained from an coding process of an algorithm of subtraction operation.

Please refer to FIG. 7. When, for example, the coding process for the check code pulse signal S3 is an algorithm of subtraction operation (−) in accordance with a third embodiment of the present invention, then the time data for the coded pulse data signal of the heartbeat signal S10 are as follows:

T1=10 ms
T2=15 ms
T3=5 ms
T4=10 ms
T5=T1−T3=10 ms−5 ms=5 ms

In this embodiment, the check code pulse signal S3 has a pulse width T5 of 5 ms. Thus, the signal transmitted by the transmitter 1 and received at the receiver 2 end would be as follows:

T1=10 ms
T2=15 ms
T3=5 ms
T4=10 ms
T5=5 ms

Similarly, the receiver 2, on receipt of the coded pulse data signal transmitted by the transmitter 1, would check the check code pulse signal S3 of the received signal according to the predetermined coding process to determine whether the received signal is a correct signal.

Figure 8:
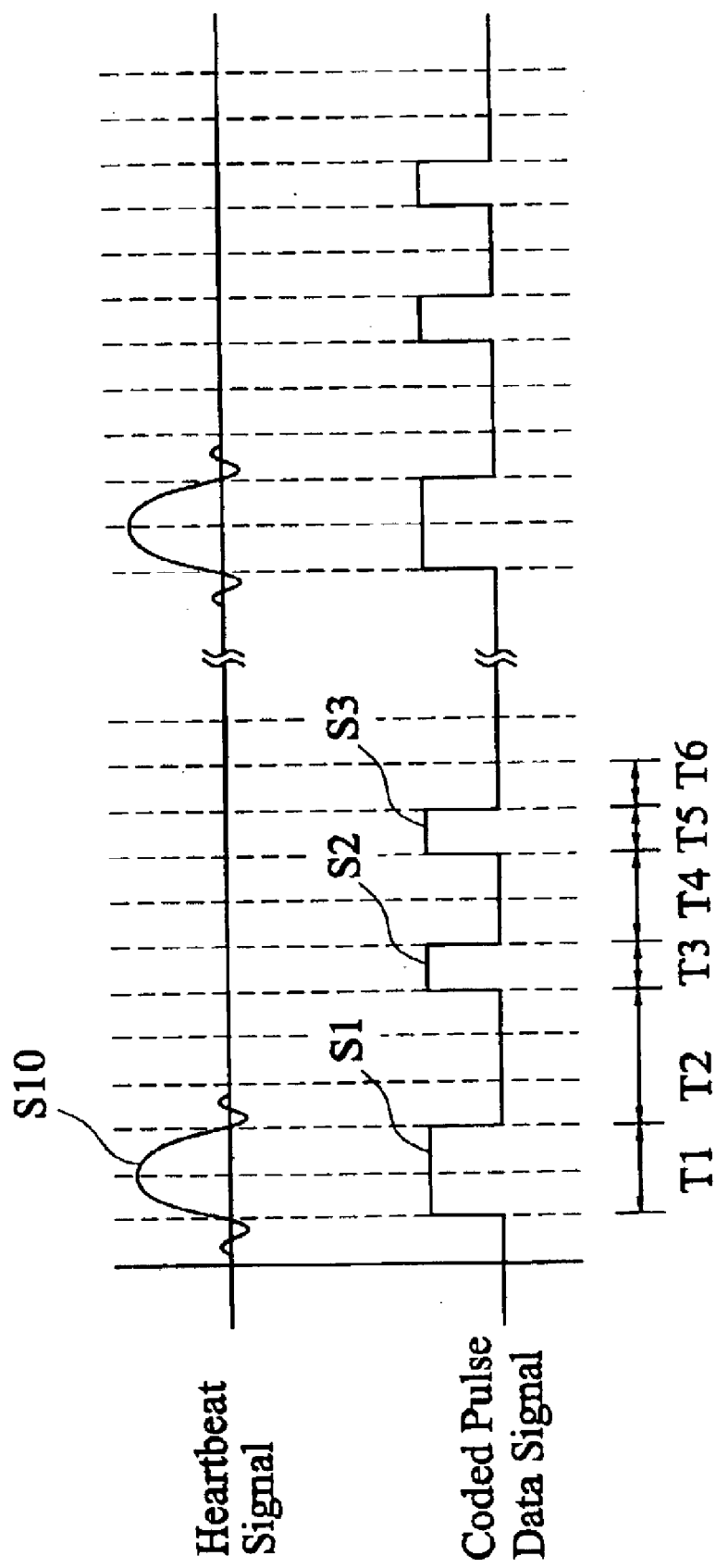
FIG. 8 shows a waveform of a pulse signal being transmitted in the form of a coded pulse signal according to a fourth embodiment of the present invention, wherein the coded pulse signal includes a check code pulse signal, which is obtained from an coding process of an algorithm of subtraction operation.

Alternatively, based on the algorithm of subtraction operation (−), the check code pulse signal S3 may be obtained by extendedly coding the pulse duration T1 of the pulse data signal S1, the time interval T2, the pulse duration T3 of the identification code pulse signal S2, and the time interval T4 in accordance with a fourth embodiment of the present invention. With reference to FIG. 8, in this embodiment, the time data for the coded pulse data signal of the heartbeat signal S10 are as follows:

T1=10 ms
T2=15 ms
T3=5 ms
T4=10 ms
T5=T1−T3=10 ms−5 ms=5 ms
T6=T2−T4=5 ms

That is, the pulse data coding processes of this embodiment comprises steps of subtracting the second duration T3 of the identification code pulse signal S2 from the first duration T1 of the pulse data signal S1 to obtain a high state pulse width T5 of the check code pulse signal S3, and subtracting the second time interval T4 from the first time interval T2 to obtain a low state pulse width T6 of the check code pulse signal S3.

Thus, the signal transmitted by the transmitter 1 and received at the receiver 2 end would be as follows:

T1=10 ms
T2=15 ms
T3=5 ms
T4=10 ms
T5=5 ms
T6=5 ms

As to other coding processes that are not described herein through application examples, such as the algorithm of multiplication, division or ratio operation, they are similar to the above-described coding processes. The coding process may, of course, be an algorithm ratio operation, such as T5=T1÷T3.

In practical applications of wireless pulse signal transmitting and receiving techniques, due to factors such as a difference between an actual and a designed distance between the transmitter and the receiver, and a circuit response rate of the receiver, the signal received at the receiver end may have a pulse width narrower than that of the signal transmitted by the transmitter. However, as long as the transmitter and the receiver are preset to work under the same predetermined coding process, any difference in pulse width between the transmitted and the received signal would not adversely affect the determination of a correctness of the check code pulse signal S3 by the receiver.

Figure 9:
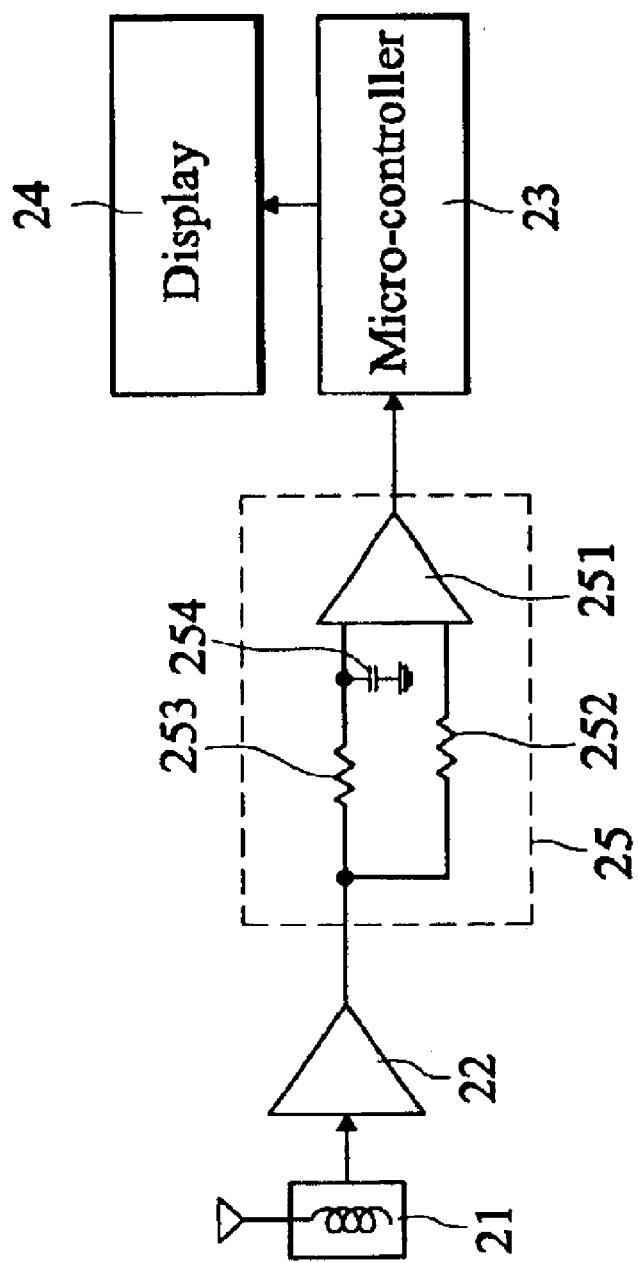
FIG. 9 is a block diagram showing the receiver of FIG. 4 includes a waveform shaping circuit incorporated therewith.

To ensure that the pulse signal received by the receiver has a pulse width that is not too narrow, a waveform shaping circuit 25 may be included in the circuitry of the receiver 2 to regulate the pulse width of the received pulse signal, as shown in FIG. 9. The waveform shaping circuit 25 mainly includes a comparator 251, a first resistance 252, a second resistance 253, and a capacitance 254. The first resistance 252 is connected between the output end of the amplification circuit 22 and an input end of the comparator 251. The second resistance 253 and the capacitance 254 together constitute a resistance-capacitance (RC) circuit to connect between the output end of the amplification circuit 22 and the other input end of the comparator 251. With the waveform shaping circuit 25, the pulse width of a signal from the output of the amplification circuit 22 may be regulated. The pulse signal having a regulated pulse width is then sent out from the output of the comparator 251 to the microcontroller 23.

Figure 10:
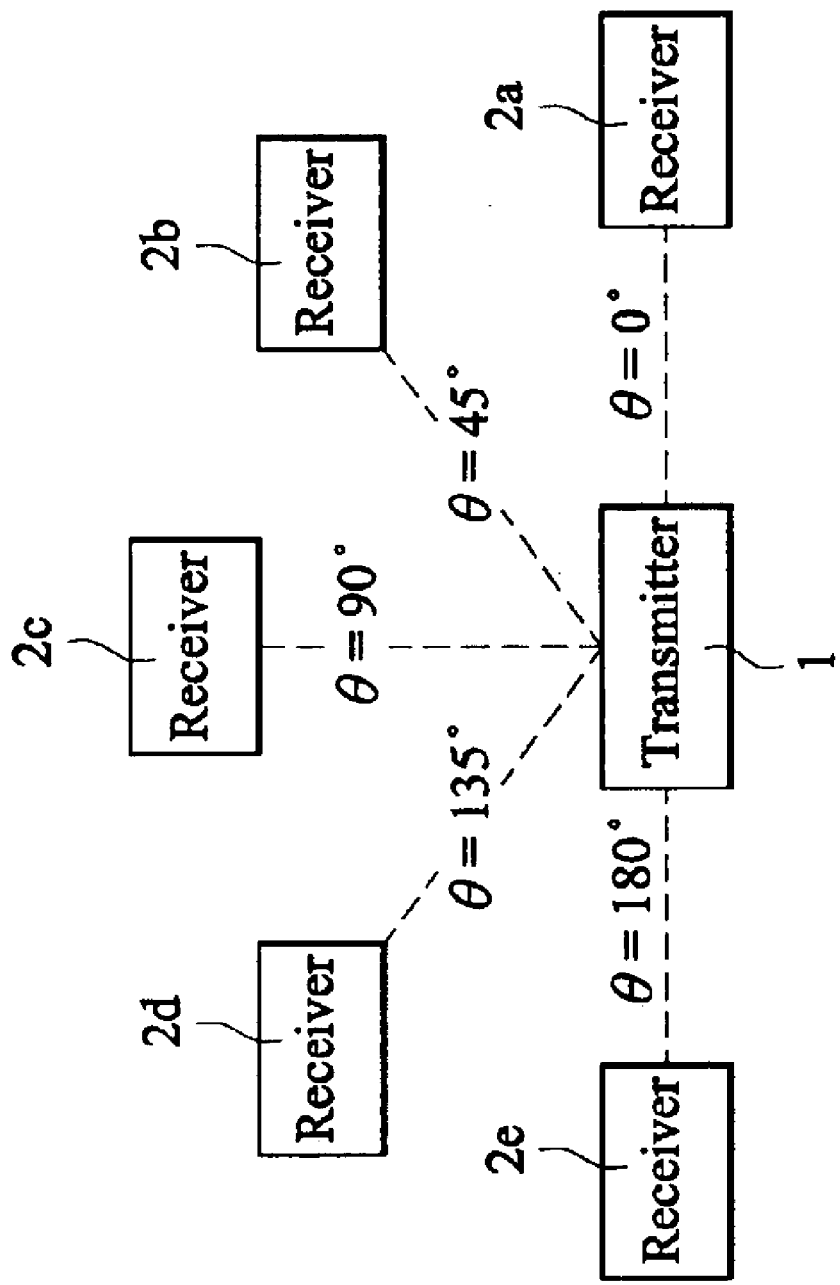
FIG. 10 shows a plurality of receivers being located at different angular positions relative to a transmitter.

In addition, in practical applications of wireless pulse signal transmitting and receiving techniques, even if the distance between the transmitter and the receiver is fixed, such as one meter, the signal received at the receiver end might still have a pulse width different from that of the signal transmitted by the transmitter due to different angular positions of the receiver relative to the transmitter. FIG. 10 shows receivers 2a, 2b, 2c, 2d, and 2e are sequentially located at different angular positions θ of 0°, 45°, 90°, 135°, and 180° relative to the transmitter 1, and FIG. 11 shows the differences in pulse width between the pulse signal transmitted by the transmitter 1 and the pulse signals received by receivers 2a, 2b, 2c, 2d, and 2e located at different angular positions θ of 0°, 45°, 90°, 135°, and 180° relative to the transmitter 1.

Figure 11:
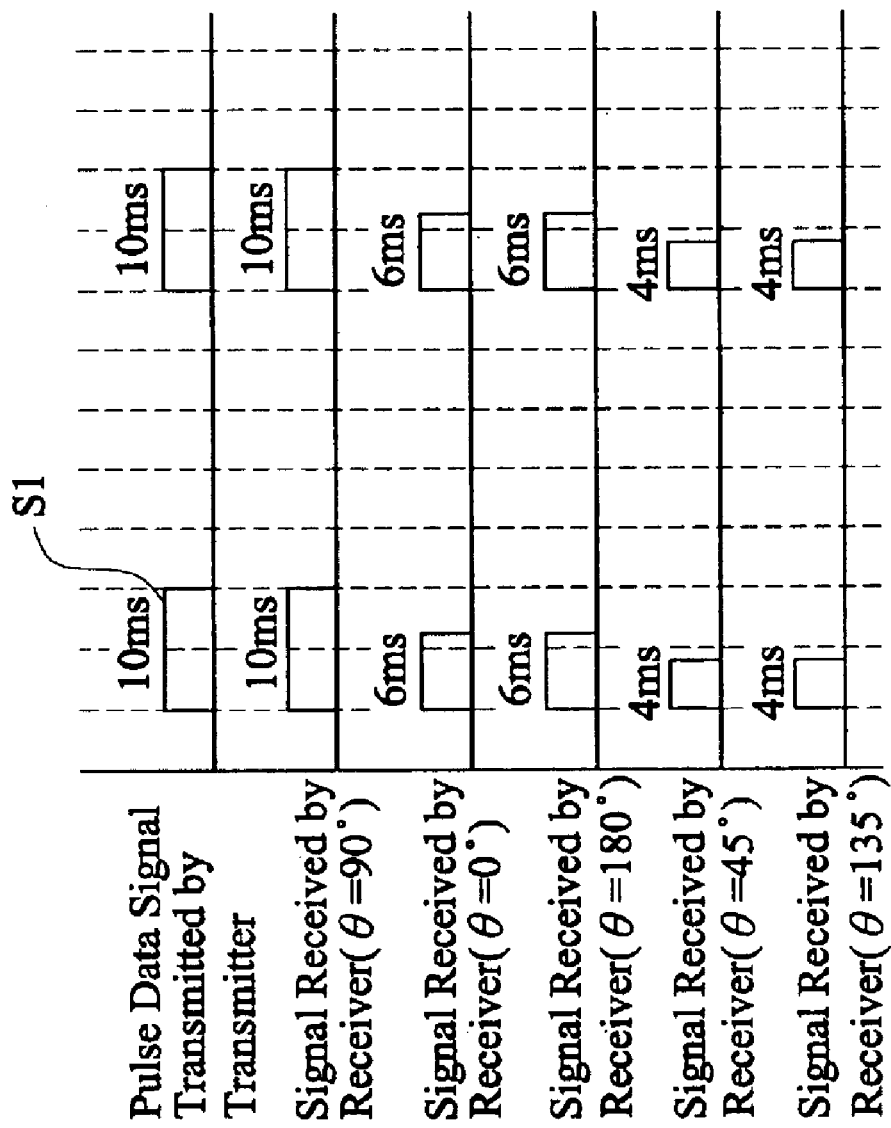
FIG. 11 shows a waveform of the differences in pulse signal width between the pulse signal transmitted by the transmitter and the pulse signals received by receivers at different angular positions relative to the transmitter.

As can be seen from FIG. 11, even if there are differences in pulse width between the pulse signal transmitted by the transmitter 1 and the pulse signals received by the receivers 2, such differences in pulse width do not adversely affect the determination of the correctness of the check code pulse signal by the receivers 2, so long as the transmitter 1 and the receivers 2 are preset to work under the same predetermined coding process.

From the above descriptions, it can be understood that the pulse data signal coded in the method of the present invention has a proportionally modulated pulse width, therefore the receiving device may still determine the correctness of the received pulse data even if the pulse width of the transmitted pulse data signal is affected by the distance and angle between the transmitter and the receiver, and/or the circuit response rate of the receiver. Moreover, since the present invention uses only three pulse signals, namely, the pulse data signal, the identification code pulse signal, and the check code pulse signal, in transmitting the pulse data and checking a correct transmission thereof, it has the advantage of reduced power consumption as compared to the conventional pulse data transmitting method that uses a plurality of coded pulses.

What is claimed is:

1. A pulse data coding method for a wireless signal transmitter and a receiver, comprising the steps of:
   (a) causing the transmitter to receive a signal of pulse data to be transmitted;
   (b) causing the transmitter to transmit the received pulse data signal having a first duration;
   (c) causing the transmitter to transmit at least one identification code pulse signal having a second duration when a first time interval lapses after the pulse data signal has been transmitted; and
   (d) causing the transmitter to transmit a check code pulse signal when a second time interval lapses after the identification code pulse signal has been transmitted; wherein the check code pulse signal is obtained by coding the pulse data signal to be transmitted and the identification code pulse signal according to a predetermined coding process, and wherein the receiver determines a correctness of a received pulse data signal transmitted by the transmitter in accordance with the coding process after receipt of the pulse data signal, the identification code pulse signal, and the check code pulse signal.

2. The pulse data coding method as claimed in claim 1, wherein the predetermined coding process comprises a step of summing the first duration of the pulse data signal and the second duration of the identification code pulse signal.

3. The pulse data coding method as claimed in claim 1, wherein the predetermined coding process comprises a step of subtracting the second duration of the identification code pulse signal from the first duration of the pulse data signal from.

4. The pulse data coding method as claimed in claim 1, wherein the predetermined coding process comprises a step of multiplying the first duration of the pulse data signal by the second duration of the identification code pulse signal.

5. The pulse data coding method as claimed in claim 1, wherein the predetermined coding process comprises a step of dividing the first duration of the pulse data signal by the second duration of the identification code pulse signal.

6. The pulse data coding method as claimed in claim 1, wherein the predetermined coding process comprises a step of obtaining a ratio of the first duration of the pulse data signal and the second duration of the identification code pulse signal.

7. The pulse data coding method as claimed in claim 1, wherein the step (d) further comprises a waveform shaping step for regulating the pulse data signal received by the receiver from the transmitter.

8. A pulse data coding method for a wireless signal transmitter and a receiver, comprising the steps of:
   (a) causing the transmitter to receive a signal of pulse data to be transmitted;
   (b) causing the transmitter to transmit the received pulse data signal having a first duration;
   (c) causing the transmitter to transmit at least one identification code pulse signal having a second duration when a first time interval lapses after the pulse data signal has been transmitted; and
   (d) causing the transmitter to transmit a check code pulse signal when a second time interval lapses after the identification code pulse signal has been transmitted; wherein the check code pulse signal is obtained by coding the first duration of the pulse data signal to be transmitted, the first time interval, the second duration of the identification code pulse signal, and the second time interval according to a predetermined coding process, and wherein the receiver determines a correctness of a received pulse data signal transmitted by the transmitter in accordance with the coding process after receipt of the pulse data signal, the identification code pulse signal, and the check code pulse signal.

9. The pulse data coding method as claimed in claim 8, wherein the coding process comprises steps of:
   (d1) summing the first duration of the pulse data signal and the second duration of the identification code pulse signal to obtain a high state pulse width of the check code pulse signal; and
   (d2) summing the first time interval and the second time interval to obtain a low state pulse width of the check code pulse signal.

10. The pulse data coding method as claimed in claim 8, wherein the coding process comprises steps of:

(d1) subtracting the second duration of the identification code pulse signal from the first duration of the pulse data signal to obtain a high state pulse width of the check code pulse signal; and (d2) subtracting the second time interval from the first time interval to obtain a low state pulse width of the check code pulse signal.

11. The pulse data coding method as claimed in claim 8, wherein the coding process comprises steps of:

(d1) multiplying the first duration of the pulse data signal and the second duration of the identification code pulse signal to obtain a high state pulse width of the check code pulse signal; and (d2) multiplying the first time interval and the second time interval to obtain a low state pulse width of the check code pulse signal.

12. The pulse data coding method as claimed in claim 8, wherein the coding process comprises steps of:

(d1) dividing the first duration of the pulse data signal by the second duration of the identification code pulse signal to obtain a high state pulse width of the check code pulse signal; and (d2) dividing the first time interval by the second time interval to obtain a low state pulse width of the check code pulse signal.

13. The pulse data coding method as claimed in claim 8, wherein the step (d) further comprises a waveform shaping step for regulating the pulse data signal received by the receiver from the transmitter.

* * * * *